(12) United States Patent
Jung et al.

(10) Patent No.: US 11,617,883 B2
(45) Date of Patent: Apr. 4, 2023

(54) MULTILAYER RING ELECTRODE HAVING A PLURALITY OF OPENINGS

(71) Applicant: Heraeus Deutschland GmbH & Co. KG, Hanau (DE)

(72) Inventors: Markus Jung, Hanau (DE); Bernd Spaniol, Hanau (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 150 days.

(21) Appl. No.: 17/374,331

(22) Filed: Jul. 13, 2021

(65) Prior Publication Data
US 2022/0008717 A1 Jan. 13, 2022

(30) Foreign Application Priority Data
Jul. 13, 2020 (DE) ..................... 10 2020 118 371.2

(51) Int. Cl.
*A61N 1/05* (2006.01)
*H01R 43/16* (2006.01)
*H01R 4/60* (2006.01)

(52) U.S. Cl.
CPC ............... *A61N 1/056* (2013.01); *H01R 4/60* (2013.01); *H01R 43/16* (2013.01)

(58) Field of Classification Search
CPC ........... A61N 1/056; H01R 4/60; H01R 43/16
USPC ........................................................ 439/889
See application file for complete search history.

(56) References Cited

U.S. PATENT DOCUMENTS

| | | | |
|---|---|---|---|
| 5,800,500 A | 9/1998 | Spelman et al. | |
| 6,801,809 B2 * | 10/2004 | Laske | A61N 1/056 607/122 |
| 7,364,479 B1 | 4/2008 | Deily | |
| 8,918,188 B2 | 12/2014 | Tiedtke | |
| 9,478,959 B2 * | 10/2016 | Markham | B23K 26/206 |
| 9,789,305 B2 * | 10/2017 | Frericks | A61N 1/0541 |
| 9,855,617 B2 | 1/2018 | Liang et al. | |

(Continued)

FOREIGN PATENT DOCUMENTS

| | | |
|---|---|---|
| CN | 101237419 | 8/2008 |
| CN | 110237419 | 9/2019 |

(Continued)

*Primary Examiner* — Peter G Leigh
(74) *Attorney, Agent, or Firm* — Dicke, Billig & Czaja, PLLC

(57) ABSTRACT

One aspect relates to a method for a ring electrode, including: providing an outer element with an outer tube and providing a first inner element with a first inner tube having a first core made of a sacrificial material. A material of the outer element and a material of the first inner element have a similar microstructure. A second inner element is provided with a second core made of a sacrificial material; A connection tube is formed by arranging the first inner element and the second inner element within the outer element. The first inner element and the second inner element are arranged concentrically. The composite tube is drawn in a longitudinal direction of the composite tube. The material of the outer element and the material of the first inner element maintain a simiular microstructure. A connection tube disc is seperated from the connection tube. The sacrificial material of the first core is removed and the sacrificial material of the second core is removed to obtain a contacting opening in the ring electrode.

11 Claims, 5 Drawing Sheets

(56) References Cited

U.S. PATENT DOCUMENTS

| | | |
|---|---|---|
| 10,022,536 B2 * | 7/2018 | Frericks ................ A61N 1/0551 |
| 10,491,189 B2 | 11/2019 | Marksteiner |
| 10,933,233 B2 | 3/2021 | Leitold et al. |
| 2001/0044646 A1 * | 11/2001 | Marshall ................ A61N 1/056 |
| | | 607/128 |
| 2008/0161887 A1 | 7/2008 | Hagen |
| 2008/0299309 A1 | 12/2008 | Fisk |
| 2013/0237789 A1 * | 9/2013 | Cattaneo ................ A61N 1/056 |
| | | 606/41 |
| 2013/0338745 A1 | 12/2013 | Ollivier |
| 2014/0261985 A1 | 9/2014 | Selkee |
| 2016/0303366 A1 | 10/2016 | Childers et al. |
| 2016/0324573 A1 | 11/2016 | Mickelson et al. |
| 2017/0143220 A1 | 5/2017 | Doerge et al. |
| 2017/0182310 A1 | 6/2017 | Troetzschel et al. |
| 2019/0091473 A1 | 3/2019 | Walter et al. |
| 2019/0255317 A1 * | 8/2019 | Leitold ................... A61N 1/05 |

FOREIGN PATENT DOCUMENTS

| | | |
|---|---|---|
| DE | 102012107155 | 2/2014 |
| DE | 102018221135 | 6/2020 |
| EP | 1128869 | 9/2001 |
| EP | 3006152 | 4/2016 |
| EP | 3170574 | 5/2017 |
| EP | 3185248 | 6/2017 |
| EP | 3530314 | 8/2019 |
| WO | 00/27469 | 8/2000 |
| WO | 2008/0127478 | 10/2008 |
| WO | 2009/044216 | 4/2009 |
| WO | 2010/034331 | 4/2010 |

\* cited by examiner

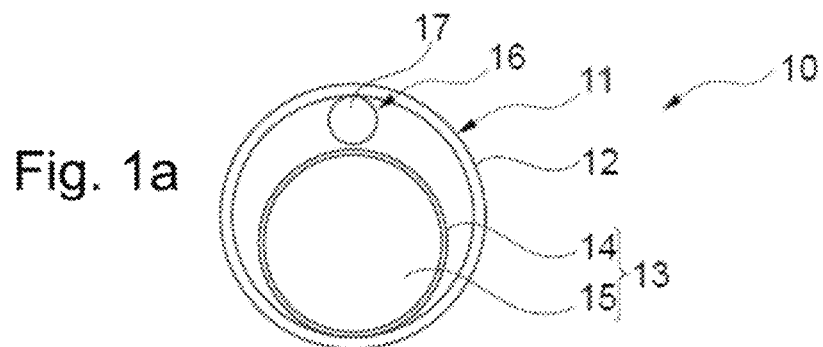
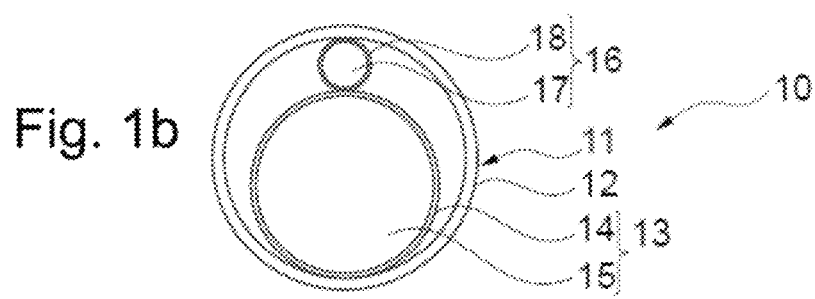
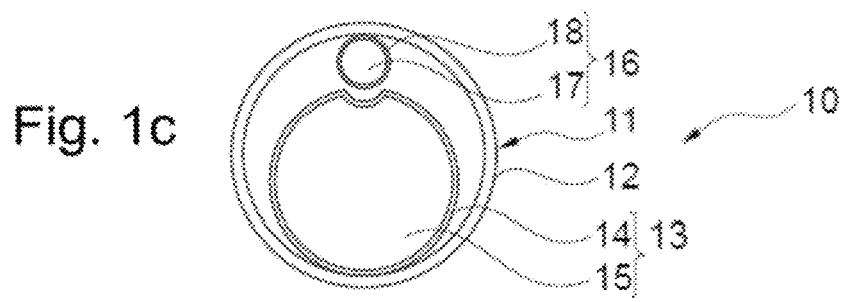
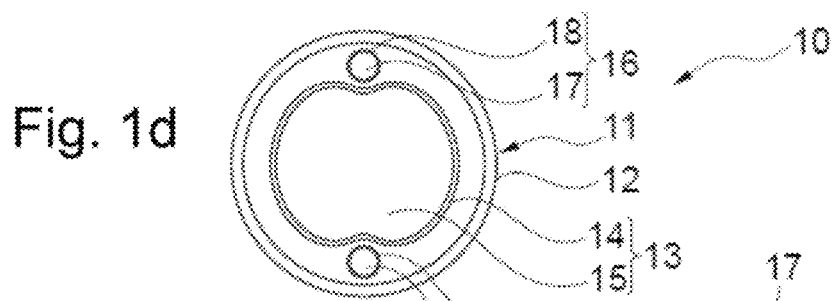
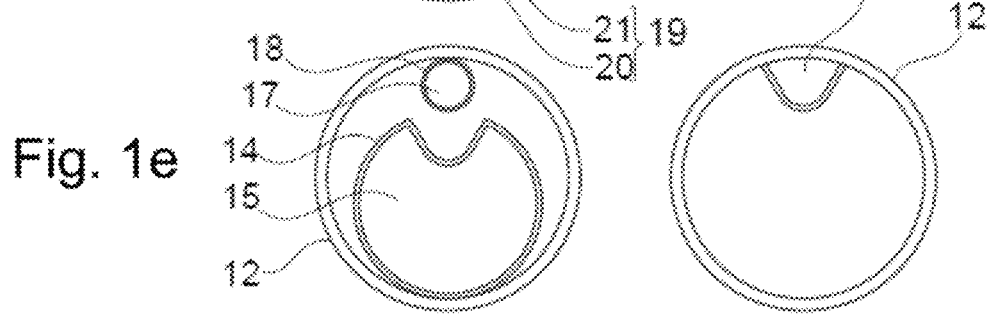

MULTILAYER RING ELECTRODE HAVING A PLURALITY OF OPENINGS

CROSS-REFERENCE TO RELATED APPLICATION

This Utility Patent Application claims priority to German Application No. 10 2020 118 371.2 filed on Jul. 13, 2020, which is incorporated herein by reference.

TECHNICAL FIELD

The embodiment relates to a manufacturing method for a ring electrode, a corresponding ring electrode, an electrode system including such a ring electrode and a use of the ring electrode or the electrode system in a cardiac pacemaker and/or for neurostimulation. The ring electrode is generally intended for use as or in an active implantable medical device, but can also be used otherwise. It can be used for signal detection and/or stimulation.

BACKGROUND

The typically very small component size of a ring electrode for an active implantable medical device and the even smaller dimensions of its partial features require very expensive and complex manufacturing facilities and manufacturing methods having many individual operational steps. Conventionally, ring electrodes are made by machining such as turning from a rod material, and the excess material inside the ring is cleared out, for example, by spark erosion. The ring electrodes are often made of noble metal, such as platinum alloys, so that the machining and the clearing of the excess material lead to considerable noble metal losses and cost disadvantages. Ring electrodes can also be composed of a plurality of parts. In this case, there is frequently the problem of permanently and fixedly connecting such parts to one another, so that the ring electrode can also withstand continuous and/or frequent loading, for example by the action of force or heat. In the case of multilayer ring electrodes, for example, the individual layers can become detached from one another by mechanical and/or thermal loading, which is also referred to as delamination.

For these and other reasons there is a need for the present embodiment.

SUMMARY

An object of one embodiment is to resolve one or more of the problems described above and others of the prior art. For example, one embodiment enables a simple and cost-effective manufacture of ring electrodes having a plurality of openings. Furthermore, one embodiment provides multi-lumen ring electrodes having improved stability, especially resistance to delamination.

Such objects are achieved by the methods and devices described herein, especially those described in the claims.

Embodiments are described below.
1. Manufacturing method for a ring electrode, comprising the following steps:
(a) providing an outer element, which comprises an outer tube,
(b) providing a first inner element, which comprises a first inner tube having a first core made of a sacrificial material, wherein a material of said first inner tube has an equal or greater Vickers hardness compared to a material of said outer tube,
(c) providing a second inner element, which comprises a second core of a sacrificial material,
(d) forming a composite tube by arranging the first inner element and the second inner element within the outer element, wherein the first inner element and the second inner element are arranged eccentrically to one another,
(e) drawing the composite tube in a longitudinal direction of the composite tube,
(f) separating a composite tube disc from the composite tube,
(g) removing the sacrificial material of the first core, and
(h) removing the sacrificial material of the second core to obtain a contacting opening in the ring electrode.
2. Manufacturing method according to embodiment 1, wherein the mean crystal grain size of the outer tube is greater than or equal to the mean crystal grain size of the first inner tube.
3. Manufacturing method according to any of the preceding embodiments, wherein the diameter of the first inner element is greater than the diameter of the second inner element.
4. Manufacturing method according to any of the foregoing embodiments, wherein the second inner element comprises a second inner tube, which surrounds the second core, wherein the second inner element is preferably arranged between the outer element and the first inner element.
5. Manufacturing method according to embodiment 4, wherein the material of the second inner tube has a Vickers hardness equal to or greater than the material of the outer tube.
6. Manufacturing method according to embodiment 4 or 5, wherein a material of the first inner tube has a Vickers hardness equal to or greater than the material of the second inner tube.
7. Manufacturing method according to any of the preceding embodiments, wherein in step (e) the outer element and the first inner element and, where applicable, the second inner tube are each connected to one another without gaps.
8. Manufacturing method according to any of the preceding embodiments, wherein the composite tube obtained subsequent to step (e) is heated to a temperature of at least 50%, preferably at least 60% or 65% of the melting temperature of the material of the outer tube or the first inner tube, in order to interconnect the outer element and the first inner element and, where applicable, the second inner tube by means of diffusion.
9. Manufacturing method according to any of the preceding embodiments further comprising a renewed drawing of the composite tube in a longitudinal direction of the composite tube subsequent to the heating.
10. Manufacturing method according to any of the preceding embodiments, wherein the outer tube and the first inner tube, and, where applicable, the second inner tube, comprise a noble metal.
11. Manufacturing method according to any of the preceding embodiments, wherein the outer tube and the second inner tube, and, where applicable, the second inner tube, are each essentially made of the same material, or different materials.
12. Manufacturing method according to any of the preceding embodiments, wherein the sacrificial material of the first core and/or the sacrificial material of the second core comprise a non-noble metal.
13. Ring electrode manufactured according to a method according to any of the preceding embodiments.

14. Ring electrode comprising an outer element, a first inner element, and a second inner element, wherein the outer element comprises an outer tube, wherein the first inner element and the second inner element are arranged within the outer element and the first inner element and the second inner element are arranged eccentrically to one another to form a composite tube, wherein the outer element, the first inner element and the second inner element are drawn together in a longitudinal direction of the composite tube, wherein a material of the first inner tube has an equal or greater Vickers hardness compared to a material of the outer tube.
15. Ring electrode comprising an outer element, a first inner element, and a second inner element, wherein the outer element comprises an outer tube, wherein the first inner element and the second inner element are arranged within the outer element and the first inner element and the second inner element are arranged eccentrically to one another to form a composite tube, wherein the outer element, the first inner element and the second inner element are drawn together in a longitudinal direction of the composite tube, wherein a material of the first inner tube has a microstructure similar to a material of the outer tube.
16. Ring electrode according to embodiment 15, wherein a material of the first inner tube has an equal or greater Vickers hardness compared to a material of the outer tube.
17. Ring electrode according to any of embodiments 13 to 16, wherein the mean crystal grain size of the outer tube is greater than or equal to the mean crystal grain size of the first inner tube.
18. Electrode system comprising a ring electrode according to any of embodiments 13 to 16 and a conductor element, wherein the conductor element is connected to a contacting opening in the ring electrode.
19. Use of a ring electrode according to any one of embodiments 13 to 16 or an electrode system according to embodiment 18 in an implantable medical sensor or stimulator.

BRIEF DESCRIPTION OF THE DRAWINGS

Further features, advantages and possible applications of the present invention will become apparent from the following description of the exemplary embodiments and the figures. All features described and/or illustrated, per se and in any combination, form the subject matter of the invention, also independently of their composition in the individual claims or their back-references. In the figures, like reference characters designate like or similar objects.

FIGS. 1a-1f illustrate a plurality of embodiments of a step of the manufacturing method for a ring electrode.

DETAILED DESCRIPTION

Figure 2A:
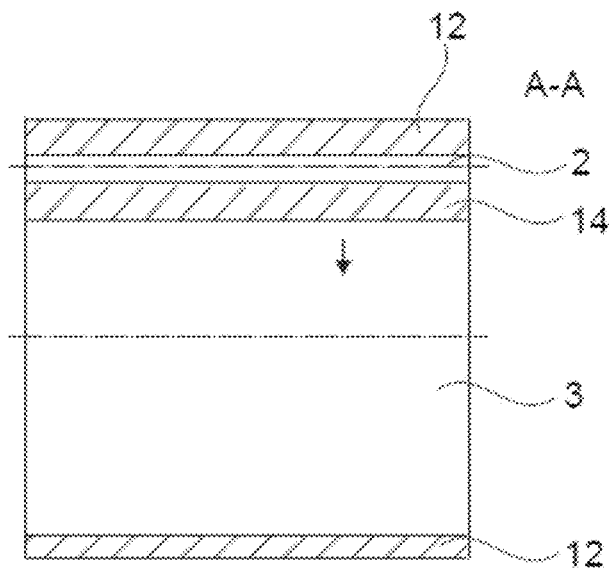
FIGS. 2a-2b illustrate exemplary longitudinal sections through a ring electrode.

In the following Detailed Description, reference is made to the accompanying drawings, which form a part hereof, and in which is illustrated by way of illustration specific embodiments in which the embodiment may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiment. The following detailed description, therefore, is not to be taken in a limiting sense, and the scope of the present embodiment is defined by the appended claims.

It is to be understood that the features of the various exemplary embodiments described herein may be combined with each other, unless specifically noted otherwise.

In principle, a further embodiment is always considered for the embodiments described herein, the elements of which basically always "have" or "comprise" a particular feature (e.g., a material), in which embodiment the element in question consists solely of the feature, i.e. it comprises no further components. The word "comprise" or "comprising" is used herein in a synonymous manner with the word "have" or "having."

If in an embodiment an element is designated with the singular, an embodiment with which a plurality of such elements are present is also considered. The use of a term for an element in the plural basically also includes an embodiment in which only a single corresponding element is contained.

Insofar as not otherwise indicated or clearly excluded from the context, it is possible in principle and is clearly considered herewith that features of different embodiments may also be present in the other embodiments described herein. It is also considered, in principle, that all features described herein in connection with a method are also applicable to the products and devices described herein, and vice versa. Strictly for reasons of brevity, all of such combinations that are considered are not explicitly listed in all cases. Technical solutions that are equivalent to the features described herein are also intended to be included within the scope of the invention.

One aspect of one embodiment relates to a manufacturing method for a ring electrode, including the following steps:
(a) providing an outer element, which includes an outer tube,
(b) providing a first inner element, which includes a first inner tube having a first core made of a sacrificial material, wherein a material of the first inner tube has an equal or greater Vickers hardness compared to a material of the outer tube,
(c) providing a second inner element, which includes a second core of a sacrificial material,
(d) forming a composite tube by arranging the first inner element and the second inner element within the outer element, wherein the first inner element and the second inner element are arranged eccentrically to one another,
(e) drawing the composite tube in a longitudinal direction of the composite tube,
(f) separating a composite tube disc from the composite tube,
(g) removing the sacrificial material of the first core, and
(h) removing the sacrificial material of the second core to obtain a contacting opening in the ring electrode.

The steps of the method may be performed in the order indicated above, or may be performed in a different order.

If the first inner tube has an equal or greater Vickers hardness compared to the outer tube, this can improve the stability of the manufactured ring electrode. Especially, delamination of the outer tube and first inner tube can be prevented or reduced.

In some embodiments, the ratio C:D is from 0.8 to 1.0; in one embodiment from 0.9 to 1.0; from 0.95 to 1.0, or from 0.99 to 1.0, wherein C is the hardness of the material of the outer tube and D is the hardness of the material of the inner tube. Vickers hardness can be determined by the testing methods described below.

A material of the outer element and a material of the first inner element may have a microstructure similar to one another. For example, the material of the outer tube and the material of the first inner tube may have a microstructure similar to one another. This means, for example, that in each case the crystal grains of a metal have a similar size and/or shape in both materials.

In some embodiments, the mean crystal grain size of the outer tube is greater than or equal to the mean crystal grain size of the first inner tube. This can improve the stability of the manufactured ring electrode. Especially, delamination of the outer tube and first inner tube can be prevented or reduced.

This can be expressed, for example, by the ratio of the respective mean crystal grain sizes of the outer tube and the first inner tube:

In one embodiment, the ratio A:B is from 1 to 1.2; in one embodiment from 1.0 to 1.1; from 1.0 to 1.05, or from 1.0 to 1.01, wherein A is the mean crystal grain size of the outer tube, and B is the mean crystal grain size of the first inner tube. The grain size can be determined with the testing methods described below.

The outer tube, the first inner tube and/or, where applicable, the second inner tube may each comprise a metal, for example a noble metal or a non-noble metal. Examples of preferred metals are Pt, Ir, Cu, Ta, Pd, Ti, Au, and alloys of such metals and multilayer material systems.

In some embodiments, the outer tube, the first inner tube and/or the second inner tube includes one or more of the metals Pt, Ir, Cu, Ta, Pd, Ti, Fe, Au, or a mixture or alloy thereof. In some embodiments, the outer tube, the first inner tube and/or the second inner tube includes one or more of the metals selected from the list consisting of Pt, Ir, Cu, Ta, Pd, Ti, Fe, Au, Mo, Nb, W, Ni, Ti, MP35N, 316L, 301 and 304.

In some embodiments, the outer tube, the first inner tube and/or the second inner tube includes the alloys PtIr10, PtIr20, or nitinol. The outer tube, the first inner tube and/or the second inner tube can also comprise multilayer material systems. In one embodiment, the outer tube, the first inner tube and/or the second inner tube includes Au, Ta, Pt, Ir, Cu, Pd or Ti. In some embodiments, the outer tube, the first inner tube and/or the second inner tube contain less than 3%, 2%, or less than 1% Fe.

MP35 is a nickel-cobalt-based hardenable alloy. A variant of MP35 is described in industry standard ASTM F562-13. In one embodiment, MP35 is an alloy including 33 to 37% Co, 19 to 21% Cr, 9 to 11% Mo and 33 to 37% Ni.

PtIr10 is an alloy made up of 88 to 92% platinum and 8 to 12% iridium.

PtIr20 is an alloy made up of 78 to 82% platinum and 18 to 22% iridium.

316L is an acid-resistant CrNiMo austenite steel with approximately 17% Cr; approximately 12% Ni and 2.0% Mo. A variant of 316L is described in the industry standard 10088-2. In one embodiment, 316L is an alloy including 16.5 to 18.5% Cr; 2 to 2.5% Mo and 10 to 13% Ni.

301 is a chromium nickel steel with high corrosion resistance. A variant of 301 is described in industry standard DIN 1.4310. In one embodiment, 301 is an alloy including 16 to 18% Cr and 6 to 8% Ni.

Nitinol is a nickel titanium alloy having shape memory and an organized cubic crystal structure and a nickel content of about 55%, wherein the remaining portion is made of titanium. Nitinol has good biocompatibility and corrosion resistance properties.

Unless otherwise stated, all percentages herein are to be understood as percent by weight (wt. %).

The outer tube, the first inner tube, and/or, where applicable, the second inner tube may each independently comprise or consist of one or more of the aforementioned metals and alloys. In one embodiment, the outer tube, the first inner tube, and/or, where applicable, the second inner tube comprise the same metal or alloy. In one embodiment, the outer tube, the first inner tube and/or, where applicable, the second inner tube each comprise different materials, for example different metals or alloys. For example, the outer tube and the first inner tube may each comprise a noble metal; or the outer tube may comprise a noble metal, while the first inner tube includes a non-noble metal. If, for example, the outer tube and the inner tube are made of the same material, an especially firm connection of such two elements can be achieved. If a plurality of elements of the ring electrode, for example the outer tube and the first inner tube, have a similar microstructure, such elements can also be connected to one another relatively fixedly if they have different materials.

An advantage of one embodiment resides in the fact that the ring electrode is manufactured not from a solid piece, such as from a bar material, but directly from hollow tubes. In this way, it is possible to dispense with a cutting or subtractive machining of the outer diameters of the tubes, and significantly less noble metal is used and lost in the interior of the ring electrode, because the tubes have no noble metal core that has to be cleared out. This eliminates not only the costs and the expense for the machining and the clearing, but also the costs of the noble metal and the noble metal losses.

The contacting opening in the ring electrode can serve for electrical and/or mechanical contacting with a conductor element. The contacting opening can thus serve as an electrical connecting element and/or as a mechanical fastening element for the conductor element. The conductor element can be a cable or a wire for contacting the ring electrode with a medical device such as a pacemaker.

The composite tube can be formed by inserting the first inner element and the second inner element into the outer element. In this case, a defined boundary surface can be produced with, for example, a defined material quality between the outer element, the first inner element and/or the second inner element. For example, a defined material quality of the boundary surface of the contacting opening for the conductor element can be created, so that the contacting of the conductor element on the ring electrode can be especially secure and reproducible, for example by crimping, clamping or inserting.

The eccentric arrangement of the first inner element and the second inner element relative to one another can be understood such that the center points or centers of mass of the two inner elements do not lie one on top of the other in cross section. The first inner element and the second inner element are therefore not arranged concentrically and therefore do not form the shape of a target disk. One inner element can at least partially cover the other inner element and the two inner elements lie next to one another, but they have no common center point or center of mass in cross section. In this way, the contacting opening can be formed such that it lies outside the center point of the ring electrode when viewed in cross section.

Drawing or drawing through can be understood to be a tensile-compressive forming, with which an output wire is brought to a reduced diameter in a plurality of steps through a drawing nozzle, drawing die or die plate. As the composite tube is drawn, the outer and inner elements can flow toward one another and reduce free spaces therebetween and possibly even close them. For example, the first inner tube can flow around the second inner element, such that the second inner element extends nose-like into the first inner tube.

The drawing makes it also possible, at least in part, to achieve a positive fit and/or a frictional connection between the individual components of the composite tube, so that an end geometry of the ring electrode is stable according to the present manufacturing method. This can be understood to mean that the individual components of the composite tube bear against one another by reciprocal mechanical blocking and/or friction. The drawing makes it also possible, at least in part, to achieve a material connection, for example by cold-sealing the individual components of the composite tube. This can be understood to mean that the individual components of the composite tube adhere to one another by chemical or atomic connection.

In one embodiment, the outer element and the first inner element are concentric with one another. This can be understood to mean that the centers or centers of mass of the outer element and of the first inner element lie one on top of the other in cross section. In this way, a cylindrical main opening of the ring electrode can be formed.

In one embodiment, the diameter of the first inner element is greater than the diameter of the second inner element. In one embodiment, the diameter of the first inner element is more than twice the diameter of the inner element. In one embodiment, the diameter of the first inner element is more than three times the diameter of the second inner element. In this way, the main opening of the ring electrode formed by the first inner element is markedly larger than the contacting opening formed by the second inner element.

In one embodiment, removing the sacrificial material of the first core includes stripping or etching. In one embodiment, removing the sacrificial material of the sacrificial material of the second core includes stripping or etching. Removing the sacrificial material of the first core and removing the sacrificial material of the second core can be performed by the same or a different type of stripping or etching. Stripping can be understood to mean the treatment of the ring electrode or its components by using a chemical stripper. Aggressive chemicals such as acids or alkalis can be used as strippers. Etching can be understood as the removal of material of the ring electrode or its components by the use of an etching agent. Chemical substances that change (usually oxidize) the material to be etched in a chemical reaction and thus bring it into solution can be used as etching agents. Etching agents may be acids or strong oxidants. The stripping or etching can be assisted by ultrasound, heat and/or electrical current.

In one embodiment, the sacrificial material of the first core is removed using an acid. In one embodiment, the sacrificial material of the second core is removed using an acid. In both cases, the same acid can, but need not, be used. The acid can be nitric acid, hydrochloric acid, hydrogen peroxide and/or the like.

In one embodiment, the second inner element includes a second inner tube that includes the second core. The second inner tube can be arranged between the outer element and the first inner element. As the composite tube is drawn, the second inner tube can be channeled into free spaces between the outer tube and the first inner tube. The second inner tube and/or the first inner tube can be soft annealed to promote this flow.

In one embodiment, the material of the second inner tube has a similar microstructure as the material of the outer tube and/or the material of the first inner tube.

In one embodiment, a material of the outer tube has a similar microstructure to a material of the second inner tube. In one embodiment, the ratio L:M is from 1 to 1.2; in one embodiment from 1.0 to 1.1; from 1.0 to 1.05, or from 1.0 to 1.01, where L is the mean crystal grain size of the outer tube, and M is the mean crystal grain size of the second inner tube.

In one embodiment, a material of the first inner tube has a similar microstructure to a material of the second inner tube. In one embodiment, the ratio H:M is from 0.8 to 1.0; in one embodiment from 0.9 to 1.0; from 0.95 to 1.0, or from 0.99 to 1.0, where H is the mean crystal grain size of the first inner tube, and M is the mean crystal grain size of the second inner tube.

In one embodiment, a material of the second inner tube has an equal or greater Vickers hardness compared to a material of the outer tube.

In some embodiments, the ratio N:P is from 0.8 to 1.0; in one embodiment from 0.9 to 1.0; from 0.95 to 1.0, or from 0.99 to 1.0, where N is the hardness of the material of the outer tube and P is the hardness of the material of the second inner tube.

In one embodiment, a material of the first inner tube has an equal or greater Vickers hardness compared to a material of the second inner tube.

In some embodiments, the ratio E:P is from 1 to 1.2; in one embodiment from 1.0 to 1.1; from 1.0 to 1.05, or from 1.0 to 1.01, where E is the hardness of the material of the first inner tube, and P is the hardness of the material of the second inner tube.

In one embodiment, the outer tube includes a noble metal or a noble metal alloy. In one embodiment, the first inner tube includes a noble metal or a noble metal alloy. In one embodiment, the optional second inner tube includes a noble metal or a noble metal alloy. The outer tube, the first inner tube and/or the second inner tube may be made of the same or different materials. Noble metals can be understood to be metals whose redox pairs have a positive standard potential with respect to the normal hydrogen electrode. The noble metal can be platinum or the like. In one embodiment, a noble metal is a metal selected from the group consisting of Ru, Rh, Pd, Ag, Os, Ir, Cu, Pt, Au and Hg. The noble metal alloy can be a platinum iridium alloy or the like, and especially a PtIr10 alloy.

In one embodiment, the sacrificial material of the first core is less noble than the material of the first inner tube. In one embodiment, the sacrificial material of the second core is less noble than the material of the first and/or second inner tube. Base metals or non-noble metals can be understood to be metals whose redox pairs have a negative standard potential with respect to the normal hydrogen electrode.

In one embodiment, the first core, made of sacrificial material, includes a non-noble metal or a non-noble metal alloy. In one embodiment, the second core of sacrificial material includes a non-noble metal or a non-noble metal alloy. An alloy made up of one or more non-noble metals or base metals can be understood as a non-noble metal alloy. The sacrificial material of the first core and the sacrificial material of the second core may be of the same or different materials or comprise it. The non-noble metal alloy can be made of or comprise copper, nickel, nickel cobalt base alloy or steel or the like or comprise it. For better dimensional stability of the (smaller) opening to be produced, the sacrificial material of the second core can be harder than the sacrificial material of the first core. In one embodiment, the first core is made of copper. In one embodiment, the second core is made of a nickel cobalt base alloy. The nickel cobalt base alloy can be MP35N (35% Ni, 35% Co, 20% Cr and 10% Mo) or MP35NLT. In one embodiment, the sacrificial material of the first core is selected from Cu, MP35N, Ni, Co, Ti, 316L, 301, 304, ceramic, or plastic. In one embodiment, the sacrificial material of the second core is selected from Cu, Ni, Co, Ti, 316L, 301, 304, ceramic, or plastic.

In one embodiment, the sacrificial material of the first core and/or the sacrificial material of the second core comprise a non-noble metal. In one embodiment, the sacrificial material of the first core and/or the sacrificial material of the second core comprise a material selected from the list consisting of Cu, MP35N, Ni, Co, Ti, 316L, 301, 304, ceramic and plastic.

The outer element, all inner elements and/or all sacrificial materials can also consist of plastics, ceramics, cermets and/or multilayer material systems. The material pairings can be chosen in any desired way, such that the sacrificial material can be more easily removed compared to the surrounding inner element.

In one embodiment, the outer element includes a material selected from the list consisting of Pt, Ir, Cu, Ta, Pd, Ti, Au, W, Mo, MP35N, 316L, 301, 304 and Nb. In one embodiment, the outer tube includes a material selected from the list consisting of Pt, Ir, Cu, Ta, Pd, Ti, Au, W, Mo, MP35N, 316L, 301, 304 and Nb.

In one embodiment, the outer element includes a non-noble metal, for example, MP35N or a stainless steel alloy. Examples of stainless steel alloys are 316L, 301 and 304. In one embodiment, the outer tube includes a non-noble metal, for example, MP35N or a stainless steel alloy.

In one embodiment, the first inner element includes a material selected from the list consisting of Pt, Ir, Cu, Ta, Pd, Ti, Au, W, Mo, MP35N, 316L, 301, 304 and Nb.

In one embodiment, the first inner tube includes a material selected from the list consisting of Pt, Ir, Cu, Ta, Pd, Ti, Au, W, Mo, MP35N, 316L, 301, 304 and Nb. In one embodiment, the first inner element includes a non-noble metal, for example, MP35N or a stainless steel alloy. In one embodiment, the first inner tube includes a non-noble metal, for example, MP35N or a stainless steel alloy.

In one embodiment, the second inner element includes a material selected from the list consisting of Pt, Ir, Cu, Ta, Pd, Ti, Au, W, Mo, MP35N, 316L, 301, 304 and Nb.

In one embodiment, the second inner tube includes a material selected from the list consisting of Pt, Ir, Cu, Ta, Pd, Ti, Au, W, Mo, MP35N, 316L, 301, 304 and Nb. In one embodiment, the second inner element includes a non-noble metal, for example, MP35N or a stainless steel alloy. In one embodiment, the second inner tube includes a non-noble metal, for example MP35N or a stainless steel alloy.

The outer tube and the first inner tube and, where applicable, the second inner tube may each consist essentially of the same material or different materials. In one embodiment, the first inner tube and the second inner tube comprise a material that in each case is selected independently from the list consisting of Pt, Ir, Cu, Ta, Pd, Ti, Au, W, Mo, MP35N, 316L, 301, 304 and Nb.

In one embodiment, the first inner tube and the second inner tube are made of a material that in each case is selected independently from the list consisting of Pt, Ir, Cu, Ta, Pd, Ti, Au, W, Mo, MP35N, 316L, 301, 304 and Nb. In one embodiment, the first inner tube and the second inner tube are made of the same material that in each case is selected independently from the list consisting of Pt, Ir, Cu, Ta, Pd, Ti, Au, W, Mo, MP35N, 316L, 301, 304 and Nb. In one embodiment, the first inner tube and the second inner tube are made of Pt or a Pt-containing alloy, for example PtIr10 or PtIr20. In one embodiment, the outer element includes a noble metal, and the first inner element and/or the second inner element includes a non-noble metal.

The degree of deformation or degree of formation can be understood as the logarithmic ratio of the length of a sample after deformation to a length of the sample prior to deformation.

In one embodiment, the composite tube is drawn with a degree of deformation of between 3 and 30% per individual draw and in one embodiment with a degree of deformation of between 3 and 20% per individual draw. In the overall connection after a plurality of or all draws, the degree of deformation can be between 50% and nearly 100%.

In one embodiment, the outer tube and/or one or all of the inner tubes are annealed prior to drawing to promote a flow of the individual tubes into spaces between the individual tubes.

In one embodiment, the outer tube and/or one or all of the inner tubes are annealed prior to drawing to promote a flow of the individual tubes into spaces between the individual tubes.

In one embodiment, the manufacturing method includes cutting the composite tube into rings after removal of the sacrificial materials. The cutting can be effected contactlessly, for example by wire erosion. For cutting, the composite tube can be fixed with a clamping device and fastened, for example, to a strip.

In one embodiment, after removal of the sacrificial materials and either before or after cutting the composite tube into rings, the manufacturing method includes further machining, which in a longitudinal section through the ring electrode reduces the length of the second inner element in relation to the outer element and/or the first inner element, so that the second inner element does not extend in the longitudinal section along the entire length of the outer element and/or the first inner element. In other words, the second inner element or the contacting opening forms at least one step in the ring electrode. This can be done by mechanical machining and/or an eroding process.

In one embodiment, prior to removal of the sacrificial materials, the manufacturing method does not include heat treatment and, especially, does not include recrystallization annealing. This has the advantage that diffusion between sacrificial materials and inner elements can be avoided. Recrystallization annealing can be understood to mean annealing without phase change at a temperature in the recrystallization range after cold forming, such as drawing. After the removal of the sacrificial materials, a heat treatment and especially a recrystallization annealing can be provided, for example in order to increase the ductility of the ring electrode.

The outer element and all the inner elements can have any desired shapes in cross section and especially be circular, oval, elliptical, semicircular, but also square, rectangular, polygonal and the like. The outer element and all the inner elements may have different cross sections from one another. In one embodiment, the outer element and all inner elements are circular in cross section.

In one embodiment, the outer tube and/or one or all of the inner tubes is a profile tube. A profile tube can be understood to be a tube that has a non-circular shape in cross section, such as, for example, a square, rectangular, semicircular or arcuate shape in cross section. In one embodiment, the first inner tube is a profile tube. The inner tube can in this case be largely circular in shape, but can have an arcuate bulge on at least one point that is designed to receive the second inner element. The profile tube can also have an arcuate bulge for a further inner element at a further location. The bulge of the profiled tube can also be trapezoidal.

Any number and arrangements of openings in a ring electrode can be produced by the manufacturing method according to the embodiments. By removing the sacrificial material of the first core, a through-hole can be formed in the ring electrode. By removing the sacrificial material of the second core, a contacting opening for electrical and/or mechanical contacting can be produced. By removing a sacrificial material of an optional third core, a further opening can be formed in the ring electrode. In one embodiment, the manufacturing method for this further includes the following steps:

providing a third inner element, which includes a third core made of a sacrificial material, forming the composite tube by arranging the third inner element within the outer element, wherein the first, second and third inner elements are arranged eccentrically to one another; and removing the sacrificial material of the third core.

The third inner element can have a third inner tube, which includes the third core made of sacrificial material. The sacrificial material of the third core can be removed as described above by stripping or etching. The further opening of the ring electrode created by removing the third core can be arranged opposite the contacting opening created by removing the second core on the outer circumference of the first inner tube. The through-hole of the ring electrode created by removing the first core can be formed in an apical shape, so that the contacting opening and the further opening can each be arranged in the opposite bulges of the apical through-hole at the outer circumference of the contacting opening.

The material of the third inner tube in one embodiment has an equal or greater Vickers hardness compared to a material of the outer tube and/or an equal or lower Vickers hardness compared to a material of the first inner tube. Especially in one embodiment, the material of the third inner tube has an equal or greater Vickers hardness compared to a material of the outer tube and an equal or lower Vickers hardness compared to a material of the first inner tube.

The material of the third inner tube can have a similar microstructure as the material of the outer tube, the material of the first inner tube, and/or the material of the second inner tube.

Correspondingly, further inner elements, each including a further inner tube and a further core of sacrificial material, can be used to produce further contacting openings.

In one embodiment, the obtained composite tube is heated subsequent to step (e) to interconnect the outer element and the first inner element and, where applicable, the second inner tube by using diffusion.

In one embodiment, the composite tube is heated subsequent to step (e) to a temperature of at least 50%, in one embodiment at least 60% or 65%, of the melting temperature of the material of the outer tube or the first inner tube, in order to interconnect the outer element and the first inner element and, where applicable, the second inner tube by using diffusion. The melting temperature, also referred to as melting point, of a material can either be obtained from the literature or be determined with simple experiments. The melting point can be determined using DSC calorimetry. A suitable device for determination is the DSC 204 F1 Phoenix by Nietzsch, Selb, Germany. The temperature described herein is measured in degrees Kelvin. For example, if the material of the outer tube has a melting point of 1500 K, a temperature of 50% of the melting temperature, in this case is 750 K. Thus, the composite tube could in this case be heated to a temperature of at least 750 K, in order to connect the outer element and the first inner element to one another by using diffusion.

In one embodiment, the heating forms a material-to-material connection of the outer element to the first inner element and, where applicable, the second inner tube.

In one embodiment, the outer element and the first inner element and, where applicable, the second inner element are connected by heating so as to form a material bond having an essentially uniform microstructure.

In one embodiment, the method further includes drawing the composite tube in a longitudinal direction of the composite tube subsequent to the heating of the composite tube described above. Drawing can be done by making smaller sized ring electrodes, as described herein, subsequent to the connection of the outer element to the inner element.

In one embodiment, the outer tube, the first inner tube, and, where applicable, the second inner tube include a noble metal.

It is further proposed to provide a ring electrode, which includes an outer element, a first inner element and a second inner element. The outer element includes an outer tube. The first inner element and the second inner element are arranged within the outer element. The first inner element and the second inner element are arranged eccentrically to one another to form a composite tube. The outer element, the first inner element, and the second inner element are drawn together in a longitudinal direction of the composite tube. The first inner element has a first inner tube surrounding a first cavity, from which a sacrificial material has been removed. The second inner element surrounds a second cavity, from which a sacrificial material has been removed and which forms a contacting opening in the ring electrode. The second inner element can be arranged between the outer element and the first inner element.

A material of the first inner tube in one embodiment has an equal or greater Vickers hardness compared to a material of the outer tube.

A material of the outer element and a material of the first inner element in one embodiment have a microstructure similar to one another.

For example, the material of the outer tube and the material of the first inner tube may have a microstructure similar to one another. This means, for example, that in each case the crystal grains of a metal have a similar size and/or shape in both materials.

In one embodiment, the ratio A:B is from 1 to 1.2; in one embodiment from 1.0 to 1.1; from 1.0 to 1.05, or from 1.0 to 1.01, wherein A is the mean crystal grain size of the outer tube, and B is the mean crystal grain size of the first inner tube. The grain size can be determined with the testing methods described below.

In some embodiments, the ratio C:D is from 0.8 to 1.0; in one embodiment from 0.9 to 1.0; from 0.95 to 1.0, or from 0.99 to 1.0, wherein C is the hardness of the material of the outer tube and D is the hardness of the material of the inner tube. Vickers hardness can be determined by the testing methods described below.

In one embodiment, the ring electrode has a boundary line, interface, or "seam" between the outer element and the first inner element when viewed in cross-section. This can be understood to mean that the outer element and the first inner element do not merge completely into one another and melt together with one another, rather, under the microscope the two elements can still be recognized as originally different components.

Some possible dimensions of the ring electrode are mentioned below. The individual dimensions are to be understood independently of one another and do not necessarily form a common embodiment, but this is possible. An outer diameter of the ring electrode, and thus an outer diameter of the outer element and the outer tube, can be between 1 and 3 mm, in one embodiment between 1.3 and 2.5 mm and in one embodiment between 1.5 and 2.0 mm. An inner diameter of the first inner element, and thus an inner diameter of the first inner tube, can be between 0.9 and 2.9 mm, in one embodiment between 1.2 and 2.4 mm and in one embodiment between 1.4 and 1.9 mm. An inner diameter of the contacting opening, and thus an outer diameter of the second core, can be between 0.10 and 0.30 mm, in one embodiment between 0.15 and 0.25 mm and in one embodiment between 0.17 and 0.20 mm.

In one embodiment, the outer diameter of the outer tube is 0.3 to 3.0 mm, in one embodiment 0.5 to 2 mm. In one embodiment, the inner diameter of the second inner tube is 0.02 to 0.3 mm, in one embodiment 0.04 to 0.2 mm. In one embodiment, the length of the ring electrode is 0.05 to 5 mm, in one embodiment 0.1 to 3 mm. In one embodiment, the wall thickness of the ring electrode is 0.005 to 0.2 mm, in one embodiment 0.01 to 0.1 mm.

It is further proposed to provide an electrode system including such a ring electrode and a conductor element. The conductor element is connected to a contacting opening in the ring electrode. The conductor element can be a wire, a cable or the like. The contacting opening in the ring electrode can be a type of small, inner hole for electrical and/or mechanical contacting of the conductor element. The contacting opening can therefore be a fastening element for the conductor element. The conductor element can be connected to the contacting opening or the fastening element of the ring electrode by welding, especially laser welding or resistance welding, soldering, crimping or the like. In this way, an especially secure and simple fastening of the conductor element to the ring electrode is achieved.

It is furthermore proposed to use such a ring electrode or such an electrode system, which were produced according to the manufacturing method described here, in a stimulator, for example a cardiac pacemaker or for neurostimulation. One embodiment can be used as a stimulation or measuring electrode for pacemaker electrodes, especially for ventricular, atrial and left ventricular leads. One embodiment can also be used for neurostimulation, for example in spinal cord stimulation, gastric stimulation, peripheral nerve stimulation or deep brain stimulation. Furthermore, use on catheters is possible, for example, in electrophysiology applications, such as for example for ablation, cardiac flow measurement or the like. Of course, other possible uses are also possible.

Examples of catheters according to one embodiment are those that are designed for electrophysiological mapping or ablation of tissue. In one embodiment, the ring electrode is configured and/or intended to be connected to a generator of an active implantable device. A ring electrode of one embodiment can also be used in a sensor, i.e. a medical device for recording an electrical signal. The electrode can also be used in a stimulator. A stimulator is a medical device that can achieve a physiological effect by emitting an electrical signal to the body of a living being. For example, a neurostimulator can cause an electrical signal in the nerve cell (e.g., an action potential) by delivering an electrical signal to a nerve cell.

A further aspect of one embodiment relates to a microelectrode or microelectrode array including a ring electrode described herein.

The ring electrodes described herein do not necessarily have to have a circular cross section. The cross section of the ring electrodes can be oval or elliptical, for example. The outer surface and the inner surface of the ring electrode in the region of the large through-hole do not necessarily have to be parallel. For example, the cross section of the outer surface can be circular and the cross section of the inner surface can be elliptical. An angular shape of the cross section is also possible in principle.

The same applies to the outer elements, inner elements and the components thereof that are used.

Testing Method

In the absence of specifically mentioned measurement conditions, all measurements are carried out under standard conditions, i.e. at a temperature of 298.15 K and an absolute pressure of 100 kPa.

Hardness

Hardness is the mechanical resistance that a material provides to the mechanical penetration of another body. Hardness can be measured by using microidentification. In this case, a Vickers diamond test specimen is pressed into the layer and the force path curve is recorded during the measurement. The mechanical parameters of the specimen, among other things hardness, can then be calculated from this curve. The determination of the hardness can be determined, for example, with the Anton Paar MHT 10 Microhardness Tester device. It should be noted that the impression depth should not be more than 10% of the layer thickness, because otherwise properties of the substrate can distort the measurements. The hardness according to Vickers can be determined according to the standard DIN EN ISO 6507-4:2018.

Grain Size

To measure crystal grain size, a first cross section of the sample to be examined is produced using metallographic methods. The grain size of the 1st cross-section is then measured using a light microscope (Leica DM4000). The light microscope is used to generate a two-dimensional first image of the grain structure of the sample. The grain size of 100 grains is measured. If the first image includes less than 100 grains, another image is generated by creating a further cross-section of the sample. The mean grain size is calculated from the arithmetic mean of the 100 grain sizes. The grain size is defined as the maximum linear distance that can be measured between 2 points on the grain boundary. For example, if the grain has an elongated shape, the grain size should be measured in the longest direction. Furthermore, the grain boundary can have a certain width. The width of the grain boundaries is not included in the determination of the grain size.

EXAMPLES

Embodiments are further illustrated below with reference to examples that, however, are not to be understood as

Example 1 (Comparative Example)

Figure 3A:
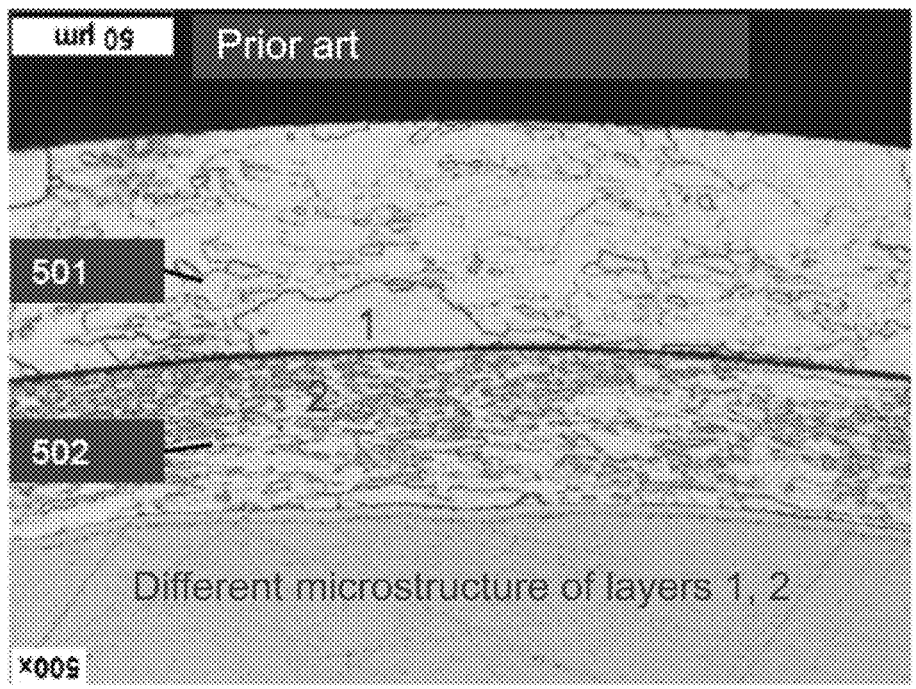
FIGS. 3a-3b illustrate microscopy images of cross sections through precursors of ring electrodes, especially their microstructure.

In contrast to the method disclosed in EP 3530314A1, a ring electrode was manufactured from an outer tube, a first inner tube and a second inner tube without the individual elements having a similar microstructure or defined hardness before being joined (see FIG. 3A). The outer tube, the first inner tube and the second inner tube were each made of PtIr10. The boundary surfaces of the individual components, i.e., the outer tube, the first inner tube and the second inner tube, were observed under the light microscope (Leica DM4000), wherein small gaps on the order of about 10 to 100 µm were observed between such components (see FIG. 4A).

Figure 5A:
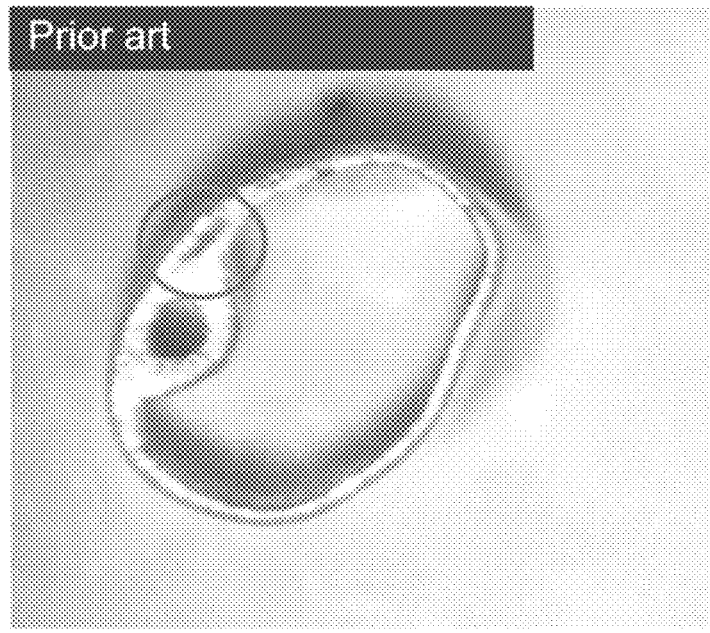
FIG. 5a-5b illustrate the result of crushing tests of ring electrodes.

The ring electrode thus produced was pinched with pliers and was slightly deformed as a result (see FIG. 5A). Delamination of the individual layers, especially separation of the outer tube from the first inner tube, was observed in this case. This resulted in an additional, undesired opening in the ring electrode.

Example 2

Figure 3B:
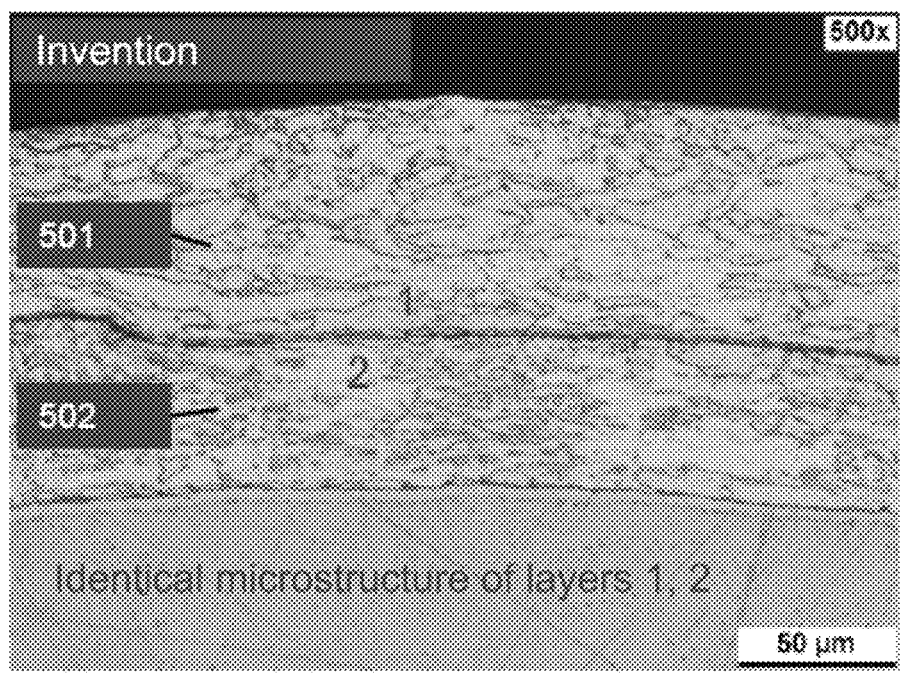

Similarly to Example 1, a ring electrode was manufactured from an outer tube, a first inner tube and a second inner tube, but a similar microstructure of such components was obtained following the cold deformation by co-annealing all of the components (see FIG. 3B). The resulting ring electrode was pinched with pliers under the same conditions as in Example 1 and thereby sharply deformed. No delamination of the individual parts was observed in this case (see FIG. 5B). The individual components, i.e. the outer tube, the first inner tube and the second inner tube, were each connected to one another without gaps (see FIG. 4B).

Example 3

The samples prepared according to Example 1 and Example 2 were each examined at various sites for their Vickers hardness.

For this purpose, impressions with a diamond tip were produced in each case in five different locations per sample (Anton Paar MHT 10 Microhardness Tester) and such impressions were measured by using a light microscope (Axiophot microscope from Zeiss). The Vickers hardness was calculated from such measured values (evaluation software test expert from Latzke).

TABLE 1

Hardness measurements in samples with which delamination was observed (samples from Example 1)

| Sample no. | Sample part | Measuring point no. | Hardness HV 0.005 |
|---|---|---|---|
| 1 | Outer tube | 1 | 224 |
| 1 | Outer tube | 2 | 222 |
| 1 | Outer tube | 3 | 229 |
| 1 | Outer tube | 4 | 224 |
| 1 | Outer tube | 5 | 228 |
| 1 | First inner tube | 1 | 204 |
| 1 | First inner tube | 2 | 207 |
| 1 | First inner tube | 3 | 215 |
| 1 | First inner tube | 4 | 209 |
| 1 | First inner tube | 5 | 211 |
| 2 | Outer tube | 1 | 222 |
| 2 | Outer tube | 2 | 221 |
| 2 | Outer tube | 3 | 224 |
| 2 | Outer tube | 4 | 228 |
| 2 | Outer tube | 5 | 228 |
| 2 | First inner tube | 1 | 210 |
| 2 | First inner tube | 2 | 200 |
| 2 | First inner tube | 3 | 213 |
| 2 | First inner tube | 4 | 216 |
| 2 | First inner tube | 5 | 222 |

TABLE 2

Hardness measurements in samples with which no delamination was observed (samples from Example 2)

| Sample no. | Sample part | Measuring point no. | Hardness HV 0.005 |
|---|---|---|---|
| 3 | Outer tube | 1 | 202 |
| 3 | Outer tube | 2 | 201 |
| 3 | Outer tube | 3 | 195 |
| 3 | Outer tube | 4 | 193 |
| 3 | Outer tube | 5 | 206 |
| 3 | First inner tube | 1 | 225 |
| 3 | First inner tube | 2 | 223 |
| 3 | First inner tube | 3 | 222 |
| 3 | First inner tube | 4 | 209 |
| 3 | First inner tube | 5 | 202 |
| 4 | Outer tube | 1 | 186 |
| 4 | Outer tube | 2 | 189 |
| 4 | Outer tube | 3 | 207 |
| 4 | Outer tube | 4 | 187 |
| 4 | Outer tube | 5 | 180 |
| 4 | First inner tube | 1 | 192 |
| 4 | First inner tube | 2 | 196 |
| 4 | First inner tube | 3 | 204 |
| 4 | First inner tube | 4 | 204 |
| 4 | First inner tube | 5 | 197 |

The figures illustrate, by way of example, various intermediate and end products of the method according to one embodiment and ring electrodes 10 according to one embodiment. The ring electrode 10 can be used as an active implantable medical device, as a sensor or stimulator, such as in a cardiac pacemaker or for neurostimulation. It can be used for signal detection and stimulation.

The manufacturing method for the ring electrode 10 here includes the following steps (not necessarily in this order):

In a step S1, providing an outer element 11, which includes an outer tube 12.

Providing a first inner element 13, which includes a first inner tube 14 having a first core 15 of a sacrificial material, wherein a material of the outer element 11 and a material of the first inner element 13 have a microstructure similar to one another.

In a step S2, providing a second inner element 16, which includes a second core 17 of a sacrificial material.

In a step S3, forming a composite tube by arranging the first inner element 13 and the second inner element 16 within the outer element 11, wherein the first inner element 13 and the second inner element 16 are arranged eccentrically to one another.

It will be apparent to those skilled in the art that other equivalent means may be similarly used in place of the features described herein.

In a step S4, drawing the composite tube in a longitudinal direction of the composite tube, wherein the material of the outer element 11 and the material of the first inner element 13 maintain a microstructure similar to one another.

In a step S5, separating a composite tube disk from the composite tube,

In a step S6, removing the sacrificial material of the first core 15 to obtain a ring electrode 10.

In a step S7, removing the sacrificial material of the second core 17 to obtain a contacting opening 2 in the ring electrode 10.

FIGS. 1a to 1e illustrate views of a plurality of embodiments of a preliminary stage of the ring electrode 10 after step S4, i.e. after the formation of the composite tube, but prior to step S5, the drawing of the composite tube. The preliminary stage of the ring electrode 10 includes an outer element 11, a first inner element 13 and a second inner element 16, wherein a material of the outer element 11, in this case the outer tube 12, and a material of the first inner element 13, in this case the first inner tube 14 have a microstructure similar to one another.

Especially in the embodiment illustrated in FIG. 1a, the outer element 11 is circular and includes a circular outer tube 12. The first inner element 13 and the second inner element 16 are also circular and lie within the outer element 11 and its outer tube 12. The first inner element 13 and the second inner element 16 are arranged eccentrically to one another, that is to say the center points of the two inner elements are not one on top of the other. The diameter of the first inner element 13 is significantly greater than the diameter of the second inner element 16.

The first inner element 13 has a circular first inner tube 14 surrounding a likewise circular first cavity including a first sacrificial material. The second inner element 16 surrounds a circular second cavity including a second sacrificial material.

In this case, the outer tube 12 and the first inner tube 13 are made of the alloy PtIr10. In this case, the first core 15 is made of copper. The second core 17 consists here of MP35N. By removing the sacrificial material of the first core 15, a through-hole 3 can be formed in the ring electrode 10 in the subsequent manufacturing step S7. Step S7 can be stripping with nitric acid in an ultrasonic bath at 80° C. By removing the sacrificial material of the second core 17, a contacting opening 2 for electrical and/or mechanical contacting can be produced in the subsequent production step S8. Step S8 can be a stripping with HCl and $H_2O_2$ in a 3:1 ratio for 15 minutes in an ultrasonic bath at 80° C. The contacting opening 2 can serve as an electrical connecting element and/or as a mechanical fastening element for a conductor element, in order to form an electrode system out of the ring electrode 10 and the conductor element.

In the embodiment illustrated in FIG. 1b, the second inner element 16 includes a second inner tube 18 including the second core 17. As the composite tube is drawn, the second inner tube 18 can be channeled into free spaces between the outer tube 12 and the first inner tube 13. The second inner tube 18 here likewise consists of PtIr10.

In the embodiments illustrated in FIGS. 1c to 1e, the first inner tube 13 is a profile tube. The inner tube 13 is largely circular in shape, but in the embodiments illustrated in FIGS. 1c and 1e has an arcuate (FIG. 1c) or trapezoidal (FIG. 1e) bulge at one location, in order to accommodate the second inner element 16.

In the embodiment illustrated in FIG. 1d, the profile tube of the first inner tube 13 has an arcuate bulge for a further, third inner element 19 at a further point opposite the second inner element 16. The third inner element 19 lies within the outer element 11 and the first, second and third inner elements are arranged eccentrically to one another. The third inner element 19 includes a third inner tube 21 and a third core 20 made of a sacrificial material, by removal of which a further opening can be produced in the ring electrode 10. In the embodiment illustrated in FIG. 1d, removing the first core 15 creates an apical through-hole 3 of the ring electrode 10, with which the contacting opening 2 and the further opening are each arranged in the opposite bulges of the apical through-hole 3.

Figure 2B:
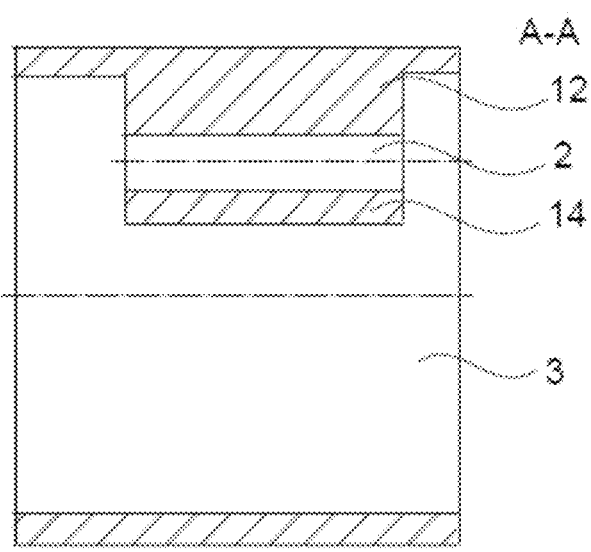

FIGS. 2a and 2b illustrate exemplary longitudinal sections through a longitudinal direction of ring electrode 10. FIG. 2a illustrates a ring electrode 10 having a constant inner diameter. FIG. 2b illustrates a ring electrode 10 having an asymmetric and stepped inner diameter. The second inner element 16 is reduced in length with respect to the outer element 11, so that the second inner element 16 and thus the contacting opening 2 do not extend in the longitudinal section along the entire length of the outer element 11. In the ring electrode 10 illustrated in FIG. 2b, the contacting opening 2 ends at its two ends within the outer element 11 of the ring electrode 10, i.e. the contacting opening 2 does not terminate flush with the ring electrode 10 at any end.

FIG. 3a is an enlarged cross section of a ring electrode preliminary stage, with which the material of the outer tube 501 and the material of the first inner tube 502 have a different microstructure. The illustrated ring electrode was prepared in accordance with Example 1.

FIG. 3b is an enlarged cross section of a preliminary stage of a ring electrode prepared by Example 2. In this case, the material of the outer tube 501 and the material of the first inner tube 502 have a microstructure similar to one another.

Figure 4A:
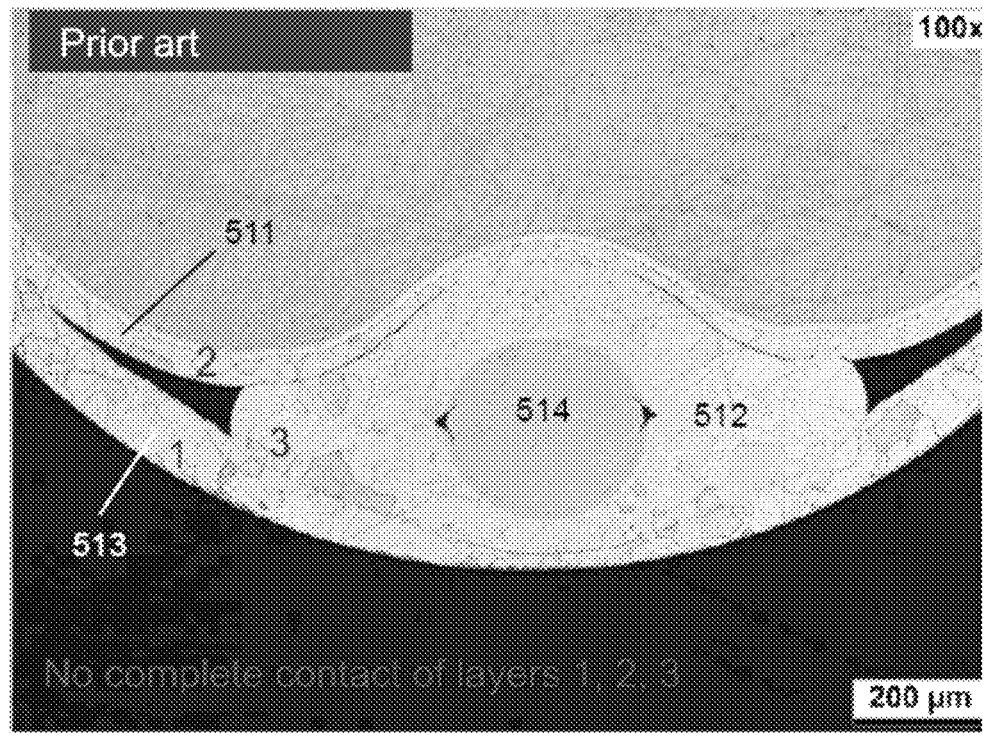
FIGS. 4a-4b illustrate further microscopy images of cross sections by precursors of ring electrodes, especially the connection of the various components.

FIG. 4a is a cross section of the preliminary stage of a ring electrode illustrated in FIG. 3a with less enlargement. In this case, larger gaps between the outer tube 513 and the first inner tube 511 can be seen. Gaps are also visible between the second inner tube 512 and the second core 514.

Figure 4B:
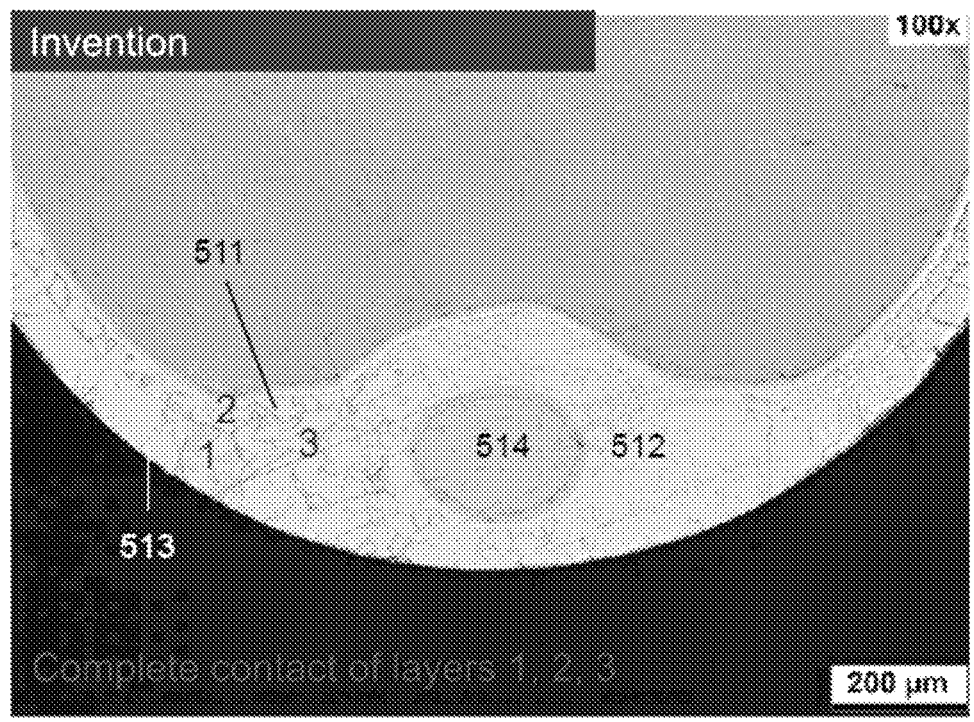

FIG. 4b illustrates a cross section of a preliminary stage of a ring electrode prepared as Example 2. In this case, no gaps can be seen between the outer tube 513 and the first inner tube 511. Also, no gaps are visible between the second inner tube 512 and the second core 514. The outer tube 513 has formed a completely positive material bond with the first inner tube 511 and the second inner tube 512 without spaces therebetween.

FIG. 5a illustrates a ring electrode manufactured according to Example 1 after performance of a crushing test using pliers. In addition to the through-hole formed by removing the first core and the contacting hole formed by removing the second core, another opening is formed by delamination of the outer tube from the first inner tube.

Figure 5B:
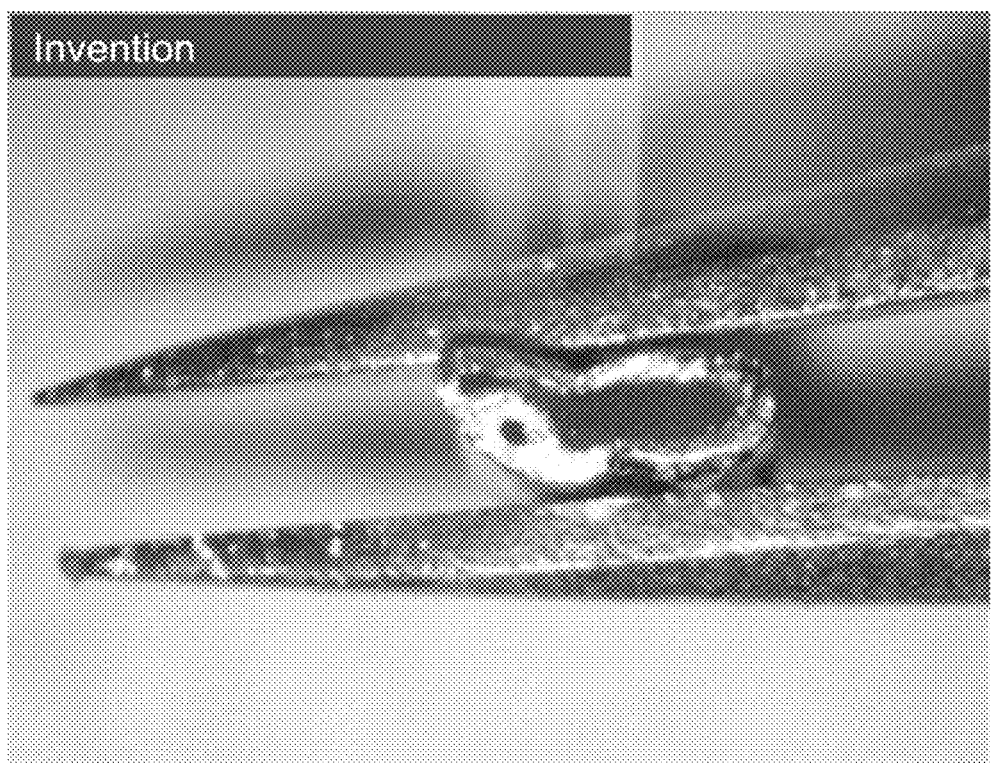

FIG. 5b illustrates a ring electrode made according to Example 1 after performance of a crushing test using pliers. In this case, the individual components of the ring electrode have not detached from one another, and the desired structure having a through-hole and a contacting hole has also been maintained after the crushing test.

In addition, it is to be understood that "comprising" or "having" does not exclude other elements or steps, and "a" or "one" does not exclude a plurality. Furthermore, it should be pointed out that features or steps that have been described with reference to one of the above exemplary embodiments can also be used in combination with other characteristics or steps of other exemplary embodiments described above. Reference characters in the claims are not to be interpreted as limitations.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiment. This application is intended to cover any adaptations or variations of the specific embodiments discussed herein. Therefore, it is intended that this embodiment be limited only by the claims and the equivalents thereof.

The invention claimed is:

1. A manufacturing method for a ring electrode, comprising:
   (a) providing an outer element, which comprises an outer tube,
   (b) providing a first inner element, which comprises a first inner tube having a first core made of a first sacrificial material, wherein a material of said first inner tube has an equal or greater Vickers hardness compared to a material of said outer tube,
   (c) providing a second inner element, which comprises a second core of a second sacrificial material,
   (d) forming a composite tube by arranging the first inner element and the second inner element within the outer element, wherein the first inner element and the second inner element are arranged eccentrically to one another,
   (e) drawing the composite tube in a longitudinal direction of the composite tube,
   (f) separating a composite tube disc from the composite tube,
   (g) removing the first sacrificial material of the first core, and
   (h) removing the second sacrificial material of the second core (17) to obtain a contacting opening in the ring electrode.

2. The manufacturing method according to claim 1, wherein the mean crystal grain size of the outer tube is greater than or equal to the mean crystal grain size of the first inner tube.

3. The manufacturing method according to claim 1, wherein the diameter of the first inner element is greater than the diameter of the second inner element.

4. The manufacturing method according to claim 1, wherein the second inner element comprises a second inner tube, which surrounds the second core.

5. The manufacturing method according to claim 4, wherein the material of the second inner tube has a Vickers hardness equal to or greater than the material of the outer tube.

6. The manufacturing method according to claim 5, wherein a material of the first inner tube has a Vickers hardness equal to or greater than material of the second inner tube.

7. The manufacturing method according to claim 1, wherein in step (e) the outer element and the first inner element and, where applicable, the second inner tube are each connected to one another without gaps.

8. The manufacturing method according to claim 1, wherein the obtained composite tube is heated subsequently to (e) to a temperature of at least 50%, preferably at least 60% or 65% of the melting temperature of the material of the outer tube or of the first inner tube, in order to interconnect the outer element and the first inner element and, where applicable, the second inner tube by means of diffusion.

9. The manufacturing method according to claim 1, wherein the outer tube and the first inner tube and, where applicable, the second inner tube each consist essentially of the same material or different materials.

10. A ring electrode manufactured by a method according to claim 1.

11. A ring electrode comprising:
   an outer element,
   a first inner element, and
   a second inner element,
   wherein the outer element comprises an outer tube,
   wherein the first inner element and the second inner element are arranged within the outer element, and the first inner element and the second inner element are arranged eccentrically to one another to form a composite tube,
   wherein the outer element, the first inner element and the second inner element are drawn together in a longitudinal direction of the composite tube; and
   wherein a material of the first inner tube has an equal or greater Vickers hardness compared to a material of the outer tube.

* * * * *